(12) United States Patent
Rodriguez

(10) Patent No.: US 7,218,972 B2
(45) Date of Patent: May 15, 2007

(54) EXTRA STRENGTH SUTURE SLEEVE

(75) Inventor: Luis M. Rodriguez, Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 521 days.

(21) Appl. No.: 10/409,439

(22) Filed: Apr. 7, 2003

(65) Prior Publication Data

US 2004/0199234 A1  Oct. 7, 2004

(51) Int. Cl.
*A61N 1/05*  (2006.01)

(52) U.S. Cl. .................. 607/126; 606/232; 604/175

(58) Field of Classification Search ............... 607/126, 607/122, 116, 132, 149; 606/232; 604/174, 604/175
See application file for complete search history.

(56) References Cited

U.S. PATENT DOCUMENTS 3,730,187 A  *  5/1973  Reynolds .................... 604/178
4,437,475 A  *  3/1984  White ........................ 607/126
4,516,584 A  *  5/1985  Garcia ....................... 607/119
4,553,961 A  * 11/1985  Pohndorf et al. ........... 604/175
4,906,233 A  *  3/1990  Moriuchi et al. ........... 604/174
5,036,862 A  *  8/1991  Pohndorf .................... 607/122
5,107,856 A  *  4/1992  Kristiansen et al. ........ 607/126
5,129,405 A  *  7/1992  Milijasevic et al. ........ 607/116
5,242,431 A     9/1993  Kristiansen
5,397,342 A     3/1995  Heil, Jr. et al.
5,683,403 A    11/1997  Adams et al.

* cited by examiner

*Primary Examiner*—Kennedy Schaetzle
(74) *Attorney, Agent, or Firm*—Schwegman, Lundberg, Woessner, & Kluth, P.A.

(57) ABSTRACT

A tubular, polyurethane reinforced suture sleeve is disclosed. The suture sleeve comprises a tubular body and a sleeve wall. A circumference of the sleeve wall is reinforced with polyurethane or other suitable material. When the sleeve wall is reinforced in this manner, it reduces the risk of cutting through the sleeve and damaging the lead with a tightening suture.

20 Claims, 2 Drawing Sheets

EXTRA STRENGTH SUTURE SLEEVE

TECHNICAL FIELD

The present device relates generally to a suture sleeve for an implantable medical device lead and particularly, but not by way of limitation, to such a suture sleeve that is strengthened to prevent a suture from damaging the lead when securing the sleeve to the lead and the implant site.

BACKGROUND

Heart disease is a major health risk in the United States and elsewhere. One well-known treatment approach utilizes an implantable medical device, like a cardiac pacing device (i.e., a pacemaker) or a defibrillator, to manage a patient's heart rate or correct cardiac arrhythmias. An arrhythmia is generally defined as an abnormal cardiac rhythm.

A pacemaker delivers a relatively mild, periodic electrical impulse to epicardial or endocardial tissue as necessary to maintain normal sinus rhythm. In comparison to a pacemaker, an implanted defibrillator applies a much stronger electrical stimulus to the heart to "shock" it into a normal rhythm. The electrical charges for both implanted pacemakers and defibrillators are applied through electrically conductive leads that emanate from the medical device and terminate at an appropriate location on the tissue.

Suture sleeves are used to secure the implanted lead at the implant site. Suture sleeves are generally configured as tubular members, the cavity or lumen of which is adapted to sheathe the electrically conductive lead body of an implantable medical device. A suture sleeve also includes circumferential grooves adapted to receive a suture. The circumferential grooves facilitate wrapping the suture sleeve with a suture to secure the sleeve to the body of a lead and to a patient's body tissue, usually the fascia tissue of the heart. Suture sleeves are typically formed of soft, implantable elastomer material, such as silicone.

Suture sleeves come in various forms. Some come from the implantable medical device manufacturer or other distributor with the lead already sheathed by the suture sleeve, thereby eliminating the need to thread or feed the lead through the sleeve during surgery. Other suture sleeves are separate from the lead, and the lead must be fed through the sleeve. Still other suture sleeves include a slit along the longitudinal axis of the sleeve to allow the sleeve to sheathe a lead body by passing the lead through the slit into the cavity or lumen of the suture sleeve.

Once the lead body is sheathed within the suture sleeve and properly positioned at the implant site, the suture sleeve is slid down the lead body to a point near the implant site and wrapped with a suture in the circumferential groove. The suture is pulled tight and tied to longitudinally secure the suture sleeve to the lead. The suture sleeve is then sutured to body tissue. Securing a suture sleeve in this manner is important to provide permanent hemostasis and lead stabilization at the implant site.

However, because suture sleeves must be moved along the longitudinal axis of the lead body during the implantation procedure and are constructed of soft, pliable material, problems may occur. For example, because the inner lumen of a typical suture sleeve is generally cylindrical, friction due to contact between the inside of the suture sleeve and the body of the lead may cause the sleeve to stick to the lead and make it difficult or impossible to slide the sleeve along the longitudinal axis of the lead body. On other occasions, if the clinician pulls the suture too tight when securing the sleeve to the lead, the suture can cut through the soft material of the suture sleeve and the insulation surrounding the lead, thereby damaging the lead. When this happens, the lead must be replaced. Unfortunately, damage to the lead is often not detected until after the surgery is complete, thereby requiring additional surgery to correct the problem and ultimately increasing the total cost of the implantation procedure.

Thus, for these and other reasons, there is a need for a strengthened or reinforced suture sleeve that reduces the risk of a suture cutting through the sleeve and damaging the lead.

SUMMARY

According to one aspect of the invention, there is provided an elastic, tubular suture sleeve for an implantable lead comprising a tubular body, a sleeve wall and an inner lumen. As used herein, the word lumen refers to the canal, duct or cavity defined by the tubular body of the suture sleeve. Also, as used herein, a "clinician" can be a physician, physician assistant (PA), nurse, medical technologist, or any other patient health care provider.

The tubular body may further comprise at least one circumferential groove adapted to receive a suture. In a preferred embodiment, the tubular body comprises three circumferential grooves. The sleeve wall is reinforced to prevent a suture from cutting through the sleeve wall and damaging a lead when the sleeve is secured to the lead with a suture. In a preferred embodiment, the sleeve wall under the three circumferential grooves is reinforced with polyurethane. Although polyurethane is the preferred reinforcement material, other materials may suitable to reinforce the sleeve wall.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention, which is set forth in the following claims.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

In the following detailed description, reference is made to the accompanying drawings that form a part hereof, and in which are shown by way of illustration specific embodiments or examples. These embodiments may be combined, other embodiments may be utilized, and structural and logical changes may be made without departing from the spirit and scope of the present invention. The following detailed description is, therefore, not to be taken in a limiting sense, and the scope of the present invention is defined by the appended claims and their equivalents.

The present device is described with respect to a reinforced suture sleeve that reduces the risk of a suture cutting through the sleeve and damaging a lead sheathed therein.

Figure 1:
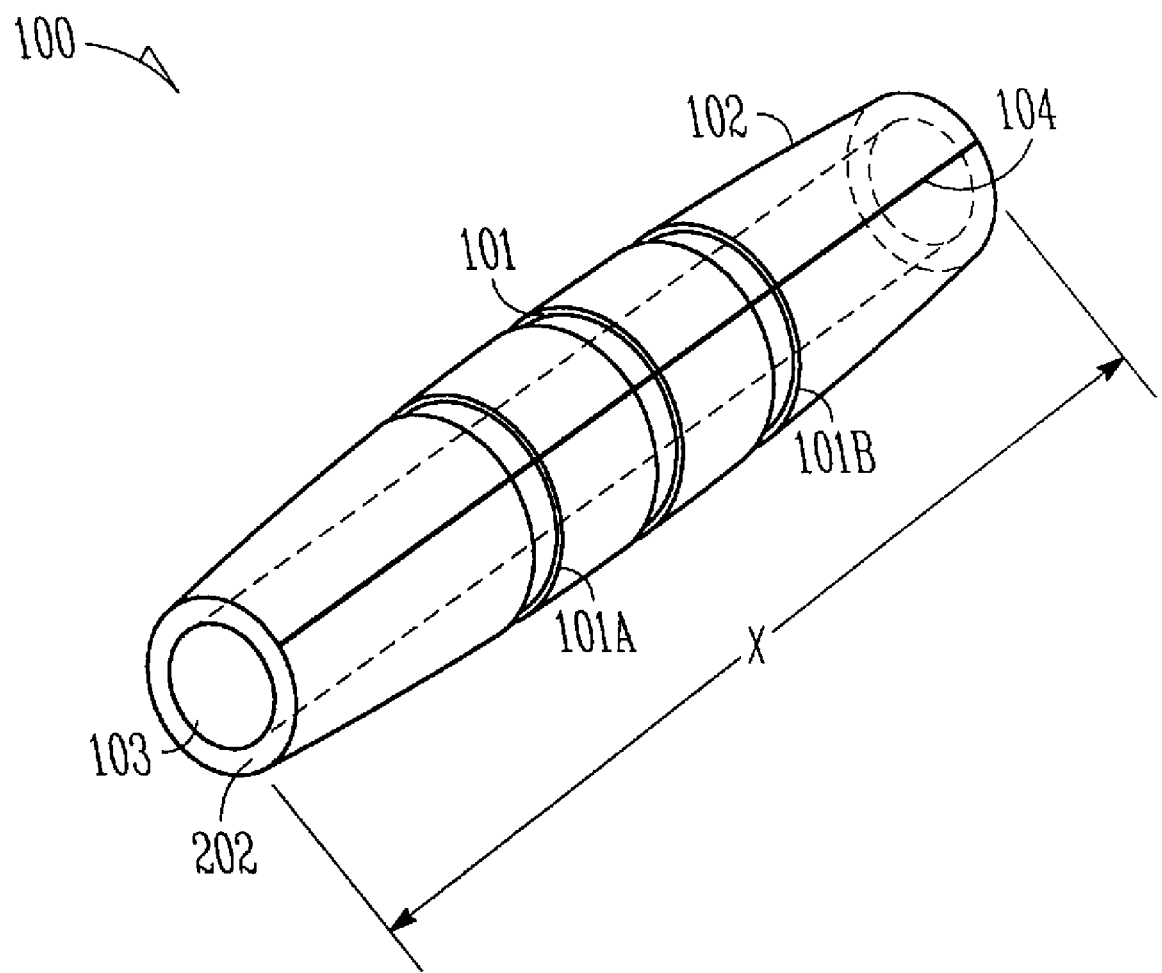
FIG. 1 is a perspective view, illustrating generally, among other things, an embodiment of a suture sleeve with a reinforced sleeve wall.

FIG. 1 is a perspective view, illustrating generally, among other things, an embodiment of a tubular, suture sleeve body 100. The tubular body 100 comprises at least one circumferential groove 101 and a suture sleeve wall 102. The tubular body 100 may comprise three circumferential grooves 101, 101a and 101b. The inside of the tubular, suture sleeve body 100 comprises an inner lumen 103 adapted to sheath or receive a lead body. The tubular body 100 may further comprise a slit 104 traversing a longitudinal axis of the suture sleeve body 100, said slit 104 adapted to receive a lead body passed there through into the inner lumen 103. The elastic nature of the suture sleeve 100 biases the slit 104 to a closed position to sheathe and retain a lead body passed through the slit 104 into the inner lumen 103. With the slit 104 in the biased, closed position, the tubular body 100 along the line of the slit is essentially contiguous.

Figure 2:
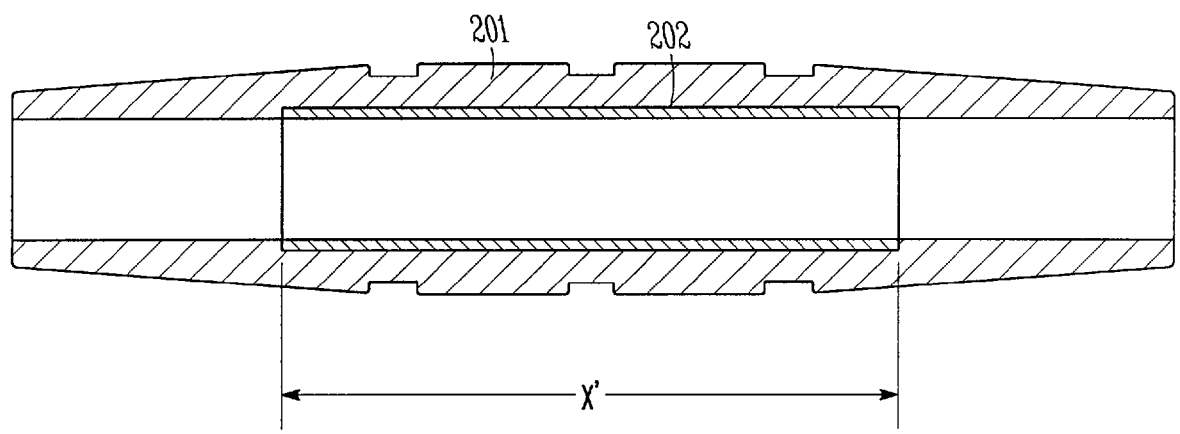
FIG. 2 is an orthogonal view, illustrating generally, among other things, an embodiment of a suture sleeve with a reinforced sleeve wall.

FIG. 2 is an orthogonal view, illustrating generally, among other things, an embodiment of a tubular, suture sleeve body 100 of a length x with a reinforced suture sleeve wall 201. The tubular body 100 and sleeve wall 201 typically comprise silicon. The sleeve wall 201 may be reinforced with at least one piece of polyurethane 202 embedded in the silicon to reinforce an entire circumference of the tubular body 100. The polyurethane 202 may traverse the entire length x of the sleeve body 100 or a portion thereof. In a preferred embodiment, an x' length of polyurethane 202 is embedded in the silicon of the sleeve wall 201 so that the entire circumference and length of the sleeve wall 201 under the circumferential grooves 101 is reinforced with polyurethane. With the sleeve wall 201 reinforced in this manner, the polyurethane protects a lead body sheathed within the inner lumen 103 from being damaged by a suture tightened around the tubular body 100. Those of skill in the art will appreciate that other materials other than polyurethane may be suitable to reinforce the sleeve wall 201 without departing from the spirit and scope of the invention.

It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including," "includes" and "in which" are used as the plain-English equivalents of the respective terms "comprising," "comprises" and "wherein."

I claim:

1. A suture sleeve for an implantable lead body comprising:
    a tubular body of a certain length further comprising a sleeve wall and an inner lumen;
    the tubular body comprising at least one suture receiving circumferential groove;
    the sleeve wall comprising a reinforcement material extending from a reinforcement first end to a reinforcement second end and embedded between the at least one suture receiving circumferential groove and the inner lumen; and
    the reinforcement first end and the reinforcement second end having a transverse cross-section completely surrounding the inner lumen.

2. The suture sleeve as recited in claim 1, wherein the tubular body comprises a plurality of suture receiving circumferential grooves.

3. The suture sleeve as recited in claim 2, wherein the plurality comprises two suture receiving circumferential grooves.

4. The suture sleeve as recited in claim 2, wherein the plurality comprises three suture receiving circumferential grooves.

5. The suture sleeve as recited in claim 1, wherein the reinforcement material comprises polyurethane.

6. The suture sleeve as recited in claim 1, wherein a length of the reinforcement material extends the length of the tubular body.

7. The suture sleeve as recited in claim 6, wherein the reinforcement material comprises polyurethane.

8. The suture sleeve recited in claim 1, wherein a length of the reinforcement material extends less than the length of the tubular body.

9. The suture sleeve as recited in claim 8, wherein the reinforcement material comprises polyurethane.

10. The suture sleeve as recited in claim 1, wherein a transverse cross-section of the inner lumen along a length of the reinforcement material is completely surrounded by the reinforcement material.

11. The suture sleeve as recited in claim 1, wherein the sleeve wall comprises silicone.

12. A suture sleeve for an implantable lead body comprising:
    a tubular body of a certain length further comprising a sleeve wall and an inner lumen;
    the tubular body comprising three suture receiving circumferential grooves
    the sleeve wall comprising a length of polyurethane embedded therein, the length of polyurethane less than the length of the tubular body, but at least about equal to a length of the tubular body portion comprising the three suture receiving circumferential grooves; and
    a transverse cross-section of the inner lumen under the three suture recieving circumferential grooves completely surrounded by the embedded polyurethane.

13. The suture sleeve as recited in claim 12, wherein the length of polyurethane comprises polyurethane tubing.

14. A suture sleeve for an implantable lead body comprising:
    a resilient tubular body of a certain length further comprising a sleeve wall and an inner lumen;
    the tubular body comprising three suture receiving circumferential grooves;
    the sleeve wall comprising a length of polyurethane less than the length of the tubular body, but at least about equal to a length of the tubular body portion comprising the three suture receiving circumferential grooves, the polyurethane embedded in the sleeve wall and extending radially around the inner lumen without interruption along the entire length thereof to reinforce an entire circumference and length of the sleeve wall under the three suture receiving circumferential grooves; and
    the sleeve wall further comprising a lead body receiving slit traversing a longitudinal axis of the tubular body and having a close position in which the tubular body along the slit is essentially contiguous.

15. The suture sleeve as recited in claim 14, wherein the sleeve wall comprises silicone and the length of polyurethane is embedded in the silicone to reinforce the entire circumference and length of the sleeve wall.

16. A suture sleeve for an implantable lead body comprising:
   a tubular body of a certain length further comprising a silicone sleeve wall and a substantially smooth lead body receiving inner lumen;
   the tubular body comprising at least two suture receiving circumferential grooves; and
   a polyurethane reinforcement material embedded in the silicone sleeve wall, the polyurethane completely surrounding the inner lumen at all radial positions between the at least two suture receiving circumferential grooves.

17. The suture sleeve as recited in claim 16, wherein a length of the polyurethane extends the length of the tubular body.

18. The suture sleeve as recited in claim 16, wherein a length of the polyurethane extends less than the length of the tubular body but at least about equal to a length of the tubular body portion comprising the at least two suture receiving circumferential grooves.

19. The suture sleeve as recited in claim 16, wherein the tubular body comprises a first, a second, and a third suture receiving circumferential groove.

20. The suture sleeve as recited in claim 16, further comprising a lead body receiving slit traversing a longitudinal axis of the tubular body.

* * * * *

UNITED STATES PATENT AND TRADEMARK OFFICE
CERTIFICATE OF CORRECTION

| | | |
|---|---|---|
| PATENT NO. | : 7,218,972 B2 | Page 1 of 1 |
| APPLICATION NO. | : 10/409439 | |
| DATED | : May 15, 2007 | |
| INVENTOR(S) | : Rodriguez | |

It is certified that error appears in the above-identified patent and that said Letters Patent is hereby corrected as shown below:

In column 4, line 44, in Claim 12, delete "recieving" and insert -- receiving --, therefor.

In column 4, line 66, in Claim 14, delete "close" and insert -- closed --, therefor.

Signed and Sealed this

Tenth Day of July, 2007

JON W. DUDAS
*Director of the United States Patent and Trademark Office*